United States Patent
Kolb et al.

(10) Patent No.: US 10,689,253 B2
(45) Date of Patent: Jun. 23, 2020

(54) PROPYLENE GLYCOL REFORMING

(71) Applicant: DIEHL AEROSPACE GMBH, Ueberlingen (DE)

(72) Inventors: Gunther Kolb, Neustadt/W. (DE); Ralf Zapf, Mainz (DE); Stefan Neuberg, Mainz (DE); Helmut Pennemann, Mainz (DE)

(73) Assignee: DIEHL AEROSPACE GMBH, Ueberlingen (DE)

( * ) Notice: Subject to any disclaimer, the term of this patent is extended or adjusted under 35 U.S.C. 154(b) by 0 days.

(21) Appl. No.: 15/899,646

(22) Filed: Feb. 20, 2018

(65) Prior Publication Data

US 2018/0237296 A1 Aug. 23, 2018

(30) Foreign Application Priority Data

Feb. 20, 2017 (DE) .................. 10 2017 001 561

(51) Int. Cl.
| | |
|---|---|
| *C01B 3/32* | (2006.01) |
| *B01J 23/63* | (2006.01) |
| *B01J 21/04* | (2006.01) |
| *B01J 23/10* | (2006.01) |
| *C07C 31/20* | (2006.01) |
| *H01M 8/0612* | (2016.01) |

(52) U.S. Cl.
CPC ............ *C01B 3/326* (2013.01); *B01J 21/04* (2013.01); *B01J 23/10* (2013.01); *B01J 23/63* (2013.01); *C07C 31/205* (2013.01); *H01M 8/0618* (2013.01); *H01M 8/0612* (2013.01)

(58) Field of Classification Search
CPC . B01J 21/04; B01J 21/06; B01J 21/063; B01J 21/08; B01J 23/10; B01J 23/40; B01J 23/42; B01J 23/755; B01J 23/892; B01J 2219/024; B01J 2219/00763; C01B 3/326; C01B 2203/0227; C07C 31/205; H01M 8/0612; H01M 8/0618

USPC ........... 502/326; 208/137–138; 422/625, 654
See application file for complete search history.

(56) References Cited

U.S. PATENT DOCUMENTS

| | | | |
|---|---|---|---|
| 4,340,501 A | 7/1982 | Davidson | |
| 5,600,053 A * | 2/1997 | Girod | ................... B01J 8/0207 |
| | | | 208/134 |
| 7,259,280 B1 | 8/2007 | Kahn et al. | |
| 2003/0054953 A1* | 3/2003 | He | ....................... B01D 53/885 |
| | | | 502/302 |
| 2008/0265212 A1 | 10/2008 | Song et al. | |
| 2009/0211942 A1* | 8/2009 | Cortright | ............. B01J 23/6567 |
| | | | 208/15 |
| 2014/0140904 A1* | 5/2014 | Kei | .......................... B01J 35/04 |
| | | | 422/654 |

FOREIGN PATENT DOCUMENTS

| | | |
|---|---|---|
| EP | 1338335 A1 | 8/2003 |
| GB | 1223695 | 3/1971 |

* cited by examiner

*Primary Examiner* — Patricia L. Hailey
(74) *Attorney, Agent, or Firm* — Scully Scott Murphy and Presser

(57) ABSTRACT

The invention relates to a catalyst for the reforming of propylene glycol, comprising a support material (1) and a catalytic constituent (2), wherein the support material (1) is composed of one or more metal oxides, and the catalytic constituent (2) comprises at least one element selected from the following group: Rh, Ru, Pd, Pt and Ni.

5 Claims, 1 Drawing Sheet

PROPYLENE GLYCOL REFORMING

Figure 1:
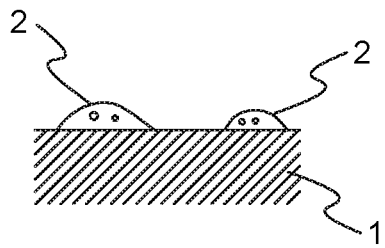

The invention relates to a catalyst for the reforming of propylene glycol and also a reformer reactor.

In a fuel cell system, electric energy is produced from hydrocarbons. For this purpose, a hydrogen-containing gas can be produced in a reformer, e.g. from propylene glycol. For this reformer reaction, propylene glycol is mixed with water, then vaporized and converted with addition of air into a hydrogen-containing gas and typically proportions of carbon monoxide, carbon dioxide, water and nitrogen. The reaction advantageously takes place as a catalytic reaction. There is a need for stable catalysts for the reforming of propylene glycol.

It is an object of the invention to eliminate the disadvantages of the prior art. In particular, a catalyst which is stable and allows complete conversion of the propylene glycol should be provided for the reforming of propylene glycol. Furthermore, a reformer reactor should be provided.

This object is achieved by the features of Claim 1. Advantageous embodiments of the invention can be derived from the features of Claims 2 to 13.

According to the invention, a catalyst for the reforming of propylene glycol, comprising a support material and a catalytic constituent, wherein the support material is composed of one or more metal oxides and the catalytic constituent comprises at least one element selected from the following group: Rh, Ru, Pd, Pt and Ni, is proposed.

The elements forming the catalytic constituent are advantageously selected from among the transition elements of transition groups VII to X of the Periodic Table. The support material has, in particular, a relatively high specific surface area in order to allow sufficient contact between the vaporized propylene glycol/water mixture and the catalyst.

The catalyst advantageously contains from 0.1 to 35% by weight, in particular from 0.5 to 20% by weight, in particular from 1 to 10% by weight, of the catalytic constituent.

The catalytic constituent is preferably selected from the group consisting of Rh, Pt and Ni. In particular, the catalytic constituent comprises Rh.

The support material is advantageously composed of at least one metal oxide of the elements Al, Si, Ti, Y, La, Ce and Pr, preferably Al, Y, La, Ce and Pr, particularly preferably Al, La and Ce. In selecting the support material, the specific surface area should be very large. At the same time, secondary reactions should be reduced or suppressed. Undesired secondary reactions include in particular formation of carbonaceous material.

It is advantageous to mix binary metal oxide mixtures in a ratio of from 1:1 to 1:1000, in particular from 1:1 to 1:100, in particular from 1:1 to 1:50. A further metal oxide can be mixed in in a ratio of from 1:10 to 1:1000. In an advantageous embodiment, the support material contains from 0 to 50% by weight of $CeO_2$, in particular from 20 to 40% by weight of $CeO_2$. $CeO_2$, as an alternative also $La_2O_3$, are used for increasing the proportion of carbon dioxide relative to carbon monoxide as reformer product.

The support material advantageously comprises $CeO_2$ and $\alpha$-$Al_2O_3$, and in particular consists of $CeO_2$ and $\alpha$-$Al_2O_3$ and unavoidable impurities. The use of $\alpha$-$Al_2O_3$ has been found to be advantageous compared to the use of $\gamma$-$Al_2O_3$: $\gamma$-$Al_2O_3$ has a higher specific surface area but also a higher acidity. A higher acidity promotes secondary reactions, in particular the formation of carbonaceous material. The formation of carbonaceous material leads to deactivation of the catalyst, so that the desired conversion of propylene glycol is reduced. Owing to the lower acidity of $\alpha$-$Al_2O_3$, secondary reactions occur to a lesser extent. Formation of carbonaceous material is largely prevented.

In an advantageous embodiment, the support material comprises $\alpha$-$Al_2O_3$ having a specific surface area of from 1 to 10 $m^2/g$.

It is advantageous for at least one of the metal oxides of the support material to be doped with an alkali metal or alkaline earth metal, in particular with Na, K and/or Mg. The metal oxide is advantageously doped with from 0.1 to 5% by weight of the doping element(s).

According to a further aspect of the invention, a reformer reactor for the reforming of propylene glycol, comprising a reactor housing having an inlet and an outlet and containing the catalyst of the invention which has been introduced as bed into the reactor housing, is proposed. A catalyst introduced as bed has a large surface area. It can if necessary be replaced with little difficulty.

According to a further aspect of the invention, a reformer reactor for the reforming of propylene glycol, comprising a reactor housing having an inlet and an outlet and containing the catalyst of the invention which has been applied as surface coating to at least part of the interior walls of the reactor housing, is proposed. An advantage of the surface coating is that the catalyst is fixed in the reformer reactor. The reformer reactor according to the invention can thus also be used, for example, in vehicles in which a bed would change or produce noises as a result of the vibrations of the vehicle.

In an alternative embodiment, a reformer reactor for the reforming of propylene glycol, comprising a reactor housing having an inlet and an outlet and containing the catalyst of the invention, wherein plates, plates having channels and/or flow-directing elements are accommodated in the reactor housing and the catalyst has been applied as surface coating to at least one of the plates, plates having channels and/or flow-directing elements, is proposed. Such a configuration allows the total coated surface area and the area occupied by the catalyst in the reactor to be increased. The surface coating can additionally have been applied to at least part of the interior walls of the reactor housing.

The surface coating is advantageously applied by one of the following methods: dip coating, spraying, jet printing or screen printing.

The invention is explained in more detail below by means of an example:

In a reformer reactor for the reforming of propylene glycol, the catalyst according to the invention is applied as wall coating by means of screen printing. Application as wall coating is particularly suitable for reformer reactors which are designed for use in vehicles. The catalyst contains essentially 5% by weight of Rh, 30% by weight of $CeO_2$ plus $\alpha$-$Al_2O_3$ and unavoidable impurities as balance. The catalyst coating has been found to be stable in the long term and allows complete conversion of the propylene glycol. Deactivation of the catalyst coating by formation of carbonaceous material on the catalyst coating is avoided in the reforming of propylene glycol. The fuel cell arrangement comprising the reformer reactor of the invention can, for example, have a power in the kilowatt range, e.g. 5 kW.

Figure 2:
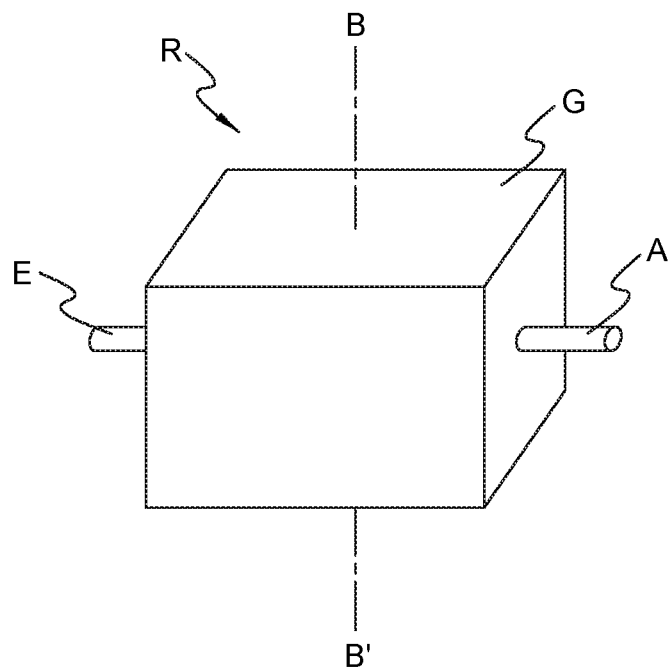
Figure 3:
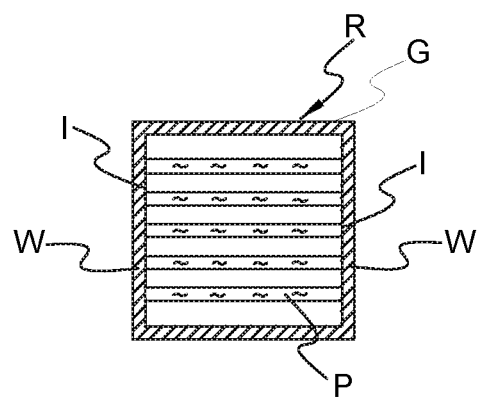
Figure 4:
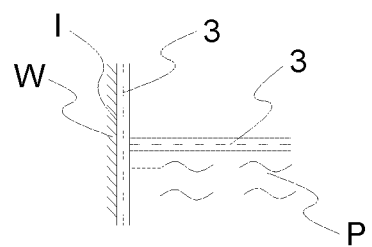

The invention is illustrated below with the aid of drawings. The drawings show:

FIG. 1 a schematic depiction of a region of the support material of a catalyst according to the invention with catalytic constituent, FIG. 2 a reformer reactor according to the invention, FIG. 3 a cross section through the reformer reactor along the line B-B' and FIG. 4 an enlarged detail of FIG. 3.

FIG. 1 schematically shows the support material 1 which is produced from metal oxide. The support material 1 has, in particular, a high specific surface area. A high specific surface area is, in particular, realized by means of an open-pored material. The catalytic constituent 2 is located on the support material 1. The catalytic constituent 2 can be present as full-area layer or as microparticles or nanoparticles distributed over the surface on the support material 1. The support material 1 is preferably uniformly coated with the catalytic constituent 2.

FIG. 2 shows a reformer reactor R. The reformer reactor R comprises a reactor housing G, an inlet E for introduction of a gas and an outlet A for discharge of a further gas. The reactor housing G comprises walls W. Plates P or flow-directing elements can be accommodated in the reactor housing G.

FIG. 3 shows a cross section along the line B-B' of FIG. 2 of the reformer reactor R. The reactor housing G is formed by walls W. The inward-directed surface of the walls W is denoted by the reference symbol I. In the reactor housing G of the reformer reactor R, plates P can, for example, be arranged horizontally above one another.

FIG. 4 shows a section of FIG. 3. This section shows an interior wall I of the wall W which is coated with a surface coating 3. Plates P present in the reactor housing G are advantageously also coated with the surface coating 3. The surface coating 3 comprises the support material 1 and the catalytic constituent 2. The surface coating 3 can be applied by means of a known coating method to the walls W and plates P or flow-directing elements which are not shown. One of the following methods is advantageously employed: dip coating, spraying, jet printing or screen printing.

LIST OF REFERENCE SYMBOLS

1 Support material
2 Catalytic constituent
3 Surface coating
A Outlet
E Inlet
G Reactor housing
I Interior wall
P Plate
R Reformer reactor
W Wall

The invention claimed is:

1. A reformer reactor for the reforming of propylene glycol, comprising a reactor housing having an inlet and an outlet and containing a catalyst comprising a support material and a catalytic constituent, wherein the support material is composed of at least one metal oxide, and the catalytic constituent comprises at least one of Ru, Rh, Pd, Pt and Ni, wherein plates are accommodated in the reactor housing and the catalyst has been applied as surface coating to at least one of the plates, the plates having channels and/or flow-directing elements, and wherein the plates are arranged horizontally, one above the other and parallel to each other.

2. The reformer reactor of claim 1 for the reforming of propylene glycol, wherein the catalyst has been introduced as bed into the reactor housing.

3. The reformer reactor of claim 1 for the reforming of propylene glycol, wherein the catalyst has been applied as surface coating to at least part of the interior walls of the reactor housing.

4. The reformer reactor according to claim 3, wherein the surface coating has been applied by one of the following methods: dip coating, spraying, jet printing or screen printing.

5. The reformer reactor according to claim 1, wherein the surface coating has been applied by one of the following methods: dip coating, spraying, jet printing or screen printing.

* * * * *